United States Patent
Yokoi et al.

(10) Patent No.: US 6,562,372 B1
(45) Date of Patent: May 13, 2003

(54) TOCOTRIENOL-CONTAINING POWDER, A PROCESS FOR PREPARING IT AND A TABLET COMPRISING COMPRESSED SAID POWDER INTO A TABLET FORM

(75) Inventors: Shinichiro Yokoi, Toyama (JP); Nobukazu Tanaka, Toyama (JP); Yoshiharu Horita, Toyama (JP); Terumasa Hosokawa, Toyama (JP); Takeshi Shishido, Toyama (JP); Heiji Ikushima, Toyama (JP)

(73) Assignee: Fuji Chemical Industry Co., Ltd., Nakaniikawa-gun (JP)

(*) Notice: Subject to any disclaimer, the term of this patent is extended or adjusted under 35 U.S.C. 154(b) by 0 days.

(21) Appl. No.: 09/509,996
(22) PCT Filed: Nov. 5, 1999
(86) PCT No.: PCT/JP99/06180
 § 371 (c)(1),
 (2), (4) Date: Apr. 5, 2000
(87) PCT Pub. No.: WO00/27393
 PCT Pub. Date: May 18, 2000

(30) Foreign Application Priority Data

Nov. 6, 1998 (JP) .......................................... 10-332054
May 6, 1999 (JP) .......................................... 11-125843

(51) Int. Cl.[7] ........................... A61K 9/20; A61K 47/00
(52) U.S. Cl. ..................... 424/464; 424/400; 424/439; 424/440; 424/441; 424/465; 424/489; 424/500; 424/502; 514/929; 514/937; 514/938; 514/939; 514/943; 514/948; 514/951; 514/960
(58) Field of Search ................................ 424/400, 439, 424/440, 441, 464, 465, 489, 500, 502; 514/929, 937, 938, 939, 943, 948, 951, 960

(56) References Cited

U.S. PATENT DOCUMENTS 5,602,183 A * 2/1997 Martin et al. ............... 514/724

FOREIGN PATENT DOCUMENTS

| JP | 64-61417 A | 3/1989 |
| JP | 1-226808 A | 9/1989 |
| JP | 2-4712 A | 1/1990 |
| JP | 8-143456 A | 6/1996 |

* cited by examiner

Primary Examiner—Thurman K. Page
Assistant Examiner—Charesse Evans
(74) Attorney, Agent, or Firm—Burns, Doane, Swecker & Mathis, LLP (57) ABSTRACT

A tocotrienol-containing powder prepared by a process wherein an oil containing a tocotrienol is treated with a lecithin, a cellulose and an emulsifying agent in water to form an emulsion, a powder substance is mixed with the formed emulsion to form a suspension and then the formed suspension is spray-dried. The powder containing tocotrienol, which has excellent storage stability and free flowability, can be used in preparing a tablet which comprises the powder compressed into a tablet form.

25 Claims, 1 Drawing Sheet

FIG. 1

TOCOTRIENOL-CONTAINING POWDER, A PROCESS FOR PREPARING IT AND A TABLET COMPRISING COMPRESSED SAID POWDER INTO A TABLET FORM

TECHNICAL FIELD

The present invention relates to a tocotrienol-containing powder which is excellent in storage stability and flowability, to a process for preparing a tocotrienol-containing powder efficiently without accompanying adhesion of it to the wall of a spray-drier in the case where its preparation is accomplished by a spray-drying method, and to a tablet comprising said powder compressed into a tablet form.

BACKGROUND TECHNOLOGY

Tocotrienol which is present in vegetable oils such as coconut oil, palm oil, rice bran oil, soybean oil and the like have been extracted and concentrated by various methods. Tocotrienol resulted from the extract of these natural materials is a mixture of plural tocotrienols.

Recently, usefulness of tocotrienol in a wide variety of fields has been studied and many examples have been reported of utilization having made in the fields of drugs, foods, cosmetics and resin composition. That is, specific utilization examples in these fields have been reported as shown below.

In the field of drugs; antisterility drug for animal, therapeutic drug for oxygen disorder (Japanese Patent Application Laid-Open No. Sho 58-96021), antitumor drug (Japanese Patent Application Laid-Open No. Sho 61-210030, therapeutic drug for hypercholesterolemia, lipemia and thrombosis (Japanese Patent Application Laid-Open No. Hei 3-246222), therapeutic drug for immunity accommodation disease, inflammation, pyrexia, edema, diabetes mellitus, pain etc. (Japanese International Patent Application Laid-Open No. Hei 7-504887), a vital aging inhibitory agent and antioxidant for composition for skin use (Japanese Patent Application Laid-Open No. Hei 8-176005), eye drops and delayed and therapeutic drug for cataract (Japanese Patent Application Laid-Open No. Hei 9-157165), poultice having blood-flow promotion action (Japanese Patent Application Laid-Open No. Hei 9-208460).

In the field of foods; nutrition food (Japanese Patent Application Laid-Open No. Sho 58-99475), antioxidant for food, use for preventing quality deterioration of food or feed by oxidation (Japanese Patent Application Laid-Open No. Hei 9-9939).

In the field of cosmetics; additive for cosmetics (Japanese Patent Application Laid-Open No. Sho 58-99475), a hair tonic (Japanese Patent Application Laid-Open Nos. Hei 8-12532 and Hei 9-157136), a deodorant and dental composition (Japanese Patent Application Laid-Open No. Hei 8-92050), skin whitening agent for external use (Japanese Patent Application Laid-Open No. Hei 8-92062), a repressing and removing agent for bad breath (Japanese Patent Application Laid-Open No. Hei 10-182388).

In the field of resin composition; an antioxidant for a polysaturated compound (Japanese Patent Application Laid-Open No. Hei 6-57247), a heat and oxidation-stabilized olefinic polymer composition wherein ascorbic acid and tocotrienols are incorporated (Japanese Patent Application Laid-Open No. Hei 8-41252)

As tocotrienols have 3 double bonds in the intramolecular side chain and are colorless to yellow, clear and oily materials, they have disadvantages that they are more sensitive to air and light than vitamin E (tocopherol) and further that blending and metering procedures with other solid substances and handling are inconvenient. Therefore, there has been a need for the development of solid or powdery tocotrienol having good storage stability.

If the hitherto proposed process for preparing powdery fat-soluble vitamins is illustrated with an example of the representative vitamin E preparation, it has been conducted by a process wherein vitamin E (or vitamin E-containing oil) is emulsified with a wide variety of emusifying agents, proteins etc., followed by the addition of an excipient, and the resultant emulsion composition is subjected to spray-drying. It has also been prepared by a process wherein vitamin E and an emulsifying agent are added to an excipient and the resultant emulsion is sprayed while granulation and drying are simultaneously accomplished. It has further been conducted by mixing vitamin E (or vitamin E-containing oil) with a carrier. More specifically, ① Japanese Patent Publication No. Hei 1-52367 discloses a process for preparing vitamin E-containing powdery saccharide wherein vitamin E and a forming agent are added to a concentrated solution of a saccharide heated to 125–165° C., which is foamed by stirring, and then the solution is cooled so that the saccharide is precipitated and water in the solution is evaporated simultaneously. ② Japanese Patent Application Laid-Open No. Sho 48-22613 discloses a process for preparing powdery vitamin E containing about 40–60% by weight of a vitamin E active compound and about 60–40% by weight of a gelatin hydrolyzate having a molecular weight of about 9,000- about 11,000 wherein an aqueous emulsion containing the vitamin E active compound, 0 Bloom and the gelatin hydrolyzate is subjected to spray-drying. ③ Japanese Patent Application Laid-Open No. Sho 60-64919 discloses a process for preparing powdery or granular vitamin E preparation wherein vitamin E is emulsified or solubilized in an aqueous phase in the presence of a saponin, an excipient is added thereto and dissolved in the resultant solution or solubilized product, which is subjected to spray-drying. ④ Japanese Patent Application Laid-Open No. Hei 8-143456 discloses a process for preparing powdery oil soluble vitamins wherein a lipid containing fat-soluble vitamins is homogeneously dispersed in a solution of an excipient containing a defatted soybean as an effective ingredient, the dispersion is mechanically emulsified, and then the resultant emulsion is subjected to a spray- or freeze-drying. Also, ⑤ Japanese Patent No.2626975 discloses a process for preparing a granule containing a vitamin E-related substance wherein the vitamin E-related substance is blended with more than 30% by weight of calcium silicate as an absorbent.

However, the above mentioned ① process involves the complicated procedure that the saccharide is precipitated, evaporating water simultaneously and causes a problem of coloration in the product. In the case where the process is conducted on a continuous and large scale, it is difficult to obtain a powder wherein vitamin E is homogeneously dispersed. The processes ② and ③ as stated above, cannot yield any powders having a good formability and sufficient flowability. In the ④ process wherein a defatted soybean is used as the excipient, the size of the powder obtained is uneven and coarse and hence its usefulness is inevitably limited. Also, the ⑤ process wherein powdery calcium silicate and vitamin E are merely blended has a problem that it takes a certain time until the mixture becomes homogeneous.

DISCLOSURE OF THE INVENTION

It is an object of the present invention to provide a tocotrienol-containing powder which has an excellent storage stability and a good flowability.

It is another object of the present invention to provide a process for preparing efficiently a tocotrienol-containing powder having a free flowability causing no adhesion of the powder to the wall of a spray-drier during its preparation step based on spray drying.

It is still another object of the present invention to provide a tablet comprising said tocotrienol-containing powder compressed into a tablet form.

In order to achieve the above objectives, the present inventors attempted previously to make tocotrienol-containing oil consisting of a mixture of plural tocotrienols resulted from the extract of the natural materials (hereinafter, referred to as tocotrienol-containing oil) powdery by application of the hitherto known process for preparing a powdery vitamin E. However, the desired powdery product could not be obtained. Even in the case where powdery product was obtained, in most cases it was difficult to recover the powdery product in a good yield from the spray chamber due to its adhesion to the wall of the spray-drier. Thus there could not be obtained any powder having a good formability, storage stability and flowability. This is considered to be mainly due to a great difficulty of obtaining pure tocotrienol on an industrial scale. Synthetic tocopherols such as vitamin E are available in the form of a substantially pure material as a raw material for preparation of powdery product. Contrary thereto, tocotrienol has not yet been commercially available in large amount as pure material. In fact, tocotrienol-containing oil extracted and concentrated from vegetable oils such as palm oil and rice bran oil has generally been used. Tocotrienols are different from tocopherols in the molecular structure, only in the presence of three double bonds in the isoprenoid side chain, and are more susceptible to undergo decomposition and change in quality under the influence of heat, light, oxygen etc. than tocopherols. For this reason, it is difficult to obtain pure tocotrienols on an industrial scale. Usually, tocotrienols are sold at the marketplace as a mixture of $\alpha$, $\beta$, $\gamma$, $\delta$-tocotrienol mixture (hereinafter, referred to as "total tocotrienol"), $\alpha$, $\beta$, $\gamma$, $\delta$-tocophenol mixture (hereinafter, referred to as the total tocopherol) and other contaminating oil component derived from the raw material. For example, the tocotrienol product (a trade name of "NuTriene tocotrienol") of Eastman Chemical Company is a mixture comprising more than 16% of the total tocotrienol (8–10% $\alpha$-tocotrienol and 8–10% $\gamma$-tocotrienol), 13–15% of the total tocopherol ($\alpha$-tocopherol) and 2–4% of other tocopherol and tocotrienol, and thus the combined content of the total tocotrienol and tocopherol being 30% or more. The molecular structure of tocotrienol and behavior of the contaminating oil components derived from the raw material are considered to adversely affect the stability of an emulsion.

As a result of having further ardently studied to achieve the foregoing objectives, the present inventors have found that there may be obtained tocotrienol-containing powder having a free flowability preventing its adhesion to the wall of a spray-drier by a process which comprises treating an oil containing a tocotrienol with a lecithin, a cellulose and an emulsifying agent in water to form an emulsion, mixing the formed emulsion with a powder substance as an oil absorbent to form a suspension and spray-drying the formed suspension, and that the obtained tocotrienol-containing powder may be compressed with the conventional tablet machine to give a tablet having an adequate hardness. The present invention has been made based on these findings.

The tocotrienol-containing powder in the present invention comprises 0.1–3.0% by weight of a lecithin, 0.1–10% by weight of a cellulose, 0.1–30% by weight of an emulsifying agent, 0.1–75% by weight, preferably 5–75% by weight, more preferably 7.5–75% by weight, the most preferably 30–75% by weight of tocotrienol and 0.1–99% by weight of a powder substance as an oil absorbent.

Furthermore, the process for preparing the tocotrienol-containing powder is characterized by the steps comprising: dissolving or suspending a lecithin, a cellulose and an emulsifying agent in water, adding an oil containing a tocotrienol to the solution or suspension under stirring to form an emulsion, adding an powder substance as an oil absorbent with the formed emulsion to form a suspension and, spray-drying the formed suspension.

The following illustrates the present invention in more details.

The present invention relates to the tocotrienol-containing powder having a good storage stability and flowability which may be prepared by a process which comprises dissolving or suspending in water (a) a lecithin, (b) a cellulose such as hydroxypropylmethylcellulose, methylcellulose, hydroxypropylcellulose, carmellose sodium or the like, and (c) an emulsifying agent such as gelatin, casein sodium, arabic gum, sodium alginate, modified starch or the like, adding (d) an oil containing a tocotrienol to the solution or suspension under a stirring to form an emulsion, adding (e) a powder substance as an oil absorbent to the formed emulsion under stirring to form a suspension and thereafter spray-drying the formed suspension.

In considering that the tocotrienol-containing powder involved in the present invention is free flowing, said powder may be prepared efficiently without causing its adhesion to the wall of a spray-drier during spray-drying.

Moreover, the tocotrienol-containing powder of the present invention has a feature that any oil components contained in it do not migrate into its surface on storage. It has a good compressibility to give a compressed mold article causing no sticking or bleeding out of the oil components when compressed to form a tablet as it is or according to the conventional manner.

As to the tocotrienol-containing powder which may be obtained in the present invention, since the surface of oil component is coated with a powder substance absorbent etc., tocotrienol present therein not only do not undergo decomposition or change in quality under the influence of heat, light etc. after spray drying, but also do not migrate to the surface of the powder even on storage for a long period of time so that it has a good storage stability and formability.

The terms "oil containing tocotrienol" mean one containing one or more of tocotrienols such as $\alpha$-, $\beta$-, $\gamma$- and $\delta$-tocotrienols as main component.

The tocotrienol as defined above may be either synthetic or naturally occurring ones. Also, they may be d-, 1- or d1-type of isomers, and the composition ratio of isomers is not limited particularly. Specific examples of tocotrienol include $\alpha$-tocotrienol such as 3,4-dihydro-2,5,7,8-tetramethyl-2-{(E,E)-4,8,12-trimethyl-3,7,11-tridecatrienyl}-2H-1-benzopyran-6-ol[synonyms: (+−)-$\alpha$-tocotrienol]3,4-dihydro-2,5,7,8-tetramethyl-2-{R(E,E)-4,8,12-trimethyl-3,7,11-tridecatrienyl}-2H-1-benzopyran-6-ol [synonyms: (R)-$\alpha$-tocotrienol],3,4-dihydro-2,5,7,8-tetramethyl-2-(4,8,12-trimethyl-3,7,11-tridecatrienyl)-2H-1-benzopyran-6-ol)(synonyms: $\alpha$-tocotrienol) and the like; $\beta$-tocotrienol such as 3,4-dihydro-2,5,8-trimethyl-2-{(E,E) 4,8,12-trimethyl-3,7,11-tridecatrienyl}-2H-benzopyran-6-ol (synonyms: $\beta$-tocotrienol) and the like; $\gamma$-tocotrienol such as 5-{3,4-dihydro-2,7,8-trimethyl-2-(4,8,12-trimethyl-3,7,11- tridecatrienyl)-2H-1-benzopyran-6-ol(γ-tocotrienol),3,3',4,4'tetrahydroxy-2,2',7,7',8,8'-hexamethyl-2,2-bis(4,8,12-trimethyl 3,7,11-tridecatrienyl)-(5,5'-bi-2H-1-benzopyran-6,6'-diol(synonyms: γ-tocotrienol),3,4-dihydro-2,7,8-trimethyl-2-{(3E,7E)-4,8,12-trimethyl-3,7,11-tridecatrienyl}-2H-1-benzopyran-6-ol(synonyms: γ-tocotrienol) and the like; and δ-tocotrienol such as 3,4-dihydro-2,8-dimethyl-2-{[(3E,7E)4,8,12-trimethyl-3,7,11-tridecatrienyl}-2H-1-benzopyran-6-ol(synonyms: δ-tocotrienol),2-(3-hydroxy-3,7,11,15-tetramethyl-6,10,14-hexadecatrienyl)-6-methyl-2,5-cyclohexadiene-1,4-dione (synonyms: δ-tocotrienol and the like.

The total tocotrienol content in the oil containing tocotrienol in the present invention may be usually 10–80% by weight, preferably 25–75% by weight, more preferably 50–75% by weight.

Also, the foregoing oil containing tocotrienol may be contain one or more of α-, β-, γ- and δ-tocotrienols derived from the raw material for preparing tocotrienol. As such oil containing tocotrienol, there may be preferably used commercially available products, for example, "NuTriene tocotrienol" (30% content, a trade name, a product of Eastman Chemical Company), "Oryzatocotrienol" (a trade name, a product of Oryza Oil & Fat Chemical Co., Ltd.), "Tocotrienol oil" (70% content, a product of Golden Hope Plantations Berhad), and "Tocotrienol oil" (30% content, 50% content, a product of Carotech Sdn Bhd.).

It is preferable that the ratio of tocotrienol content to tocopherol content in the oil containing tocotrienol is more than 1, (tocotrienol/tocopherol=>1 when expressed in ratio by weight).

Also, there may be included therein nicotinic, acetic or succinic ester of tocotrienol.

Although the content of tocotrienol in the finished powder product is not limited particularly, it may be in the range of 0.1–75% by weight, preferably 5–75% by weight, more preferably 7.5–75% by weight, the most preferably 30–75% by weight depending on the intended use. According to the present invention, even in case where it is more than 30% by weight and the maximum of 75% by weight, the desired spray-dried powder having a good storage stability and flowability can be obtained by formulating a composition comprising 30–75% by weight of oil containing tocotrienol, 0.5–3% by weight of lecithin, 1–10% by weight of cellulose, 10–30% by weight of an emulsifying agent and 10–50% by weight of a powder substance.

As lecithin which may be used in the present invention, it is phosphatidyl choline used conventionally. Examples of lecithin include vegetable lecithin, fractionated lecithin, yolk lecithin, enzyme-treated lecithin, enzyme-decomposed lecithin and the like. These lecithines may be either paste or powdery form. However, it is preferable to use lecithin which is a liquid at the ordinary temperature since it is more emulsifiable in water than the powder.

Examples of the commercial product include soyabean lecithin (a product of Wako Pure Chemical Industries, Ltd.), "SLP Paste" (a product of True Lecithin Industry Co., Ltd.), "Benecoat BMI-40", "Benecoat BMI-40L", "Benecoat BMI-60" (products of Kao Corporation) and the like.

The amount used of lecithin may be varied depending on the kind and amount of the oil containing tocotrienol used, the kind of emulsifying agent used and the concentration of a suspension to be spray-dried, thus should not be limited particularly. However, it may be usually 0.1–3% by weight, preferably 0.5–3% by weight, more preferably 0.5–2.5% by weight based on the weight of the powder composition to be fed.

If the amount used of lecithin is less than 0.1% by weight, then there can be obtained tocotrienol-containing powder. But, it does not become spherical in shape, and has a stickiness so that oil present therein bleeds out. On the other hand, if the amount used of lecithin exceeds 3% by weight, then there can be obtained undesirable sticky spray-dried powder. And therefore, it is necessary to use lecithin in a amount within the limited range as shown above.

Thus, it is an outstanding feature of the present invention that the characteristic property of the spray-dried powder is greatly influenced by adding lecithin in an amount as little as 0.1–3% by weight.

As an emulsifying agent, gelatin, casein sodium, arabic gum, sodium alginate, modified starch or mixture thereof may be preferably used from the standpoint of safety and powdering being easily accomplished. However, gelatin is particularly preferred. In addition to these emulsifying agents, there may also be employed adequately depending on the intended use of the tocotrienol-containing powder a nonionic surfactant, an anionic surfactant, a cationic surfactant(e.g. polyoxyalkylene adduct of a higher alcohol, polyoxyalkylene fatty acid ester, polyoxyalkylene glycol adduct of higher amine, polyoxyalkylene glycol adduct of polyhydric alcohol, metal salt of higher fatty acid, sodium higher alcohol sulfate, sodium higher alcohol phosphate, aliphatic quaternary ammonium salt such as polyoxyethylene lauryl dimethylammonium chloride) which are generally used in preparing an aqueous emulsion. The amount used of the emulsifying agent may be varied depending on the kind and amount of the oil containing tocotrienols used, the kind of emulsifying agent used, the concentration of a suspension to be spray-dried, thus should not be limited particularly. However, it may be usually 0.1–50% by weight, preferably 0.5–30% by weight, based on the weight of the oil containing tocotrienol used.

A cellulose is one which acts as emulsifying auxiliary material and the use of it with lecithin causes not only increasing effect of stability of emulsion but also imparting effect of non-stickiness into the spray-dried powder product. As the cellulose, it may be any of a water-soluble, water-insoluble, water-partially soluble and water-swellable ones. Examples of a water soluble cellulose include carmellose sodium (a product of Daicel Co., Ltd., a trade name of "CMC Daicel"), methylcellulose, hydroxypropylcellulose (e.g. a trade name "Nisso HPC", a product of Nippon Soda Co., Ltd., a trade name "Shin-Etsu HPC", a product of Shin-Etsu Chemical Industry Co., Ltd.), hydroxypropylmethylcellulose (e.g. trade names "HPMC -2208, -2906, -2910", products Shin-Etsu Chemical Industry Co., Ltd., a trade name "Metlose 90SH, 65SH, 60SH", products of Shin-Etsu Chemical Industry Co., Ltd., trade names "Methocel K. F. E", "Marpolose" and "TC-5", products of Dow Chemical Co., Ltd.)", hydroxyethylcellulose and the like. Examples of water-insoluble, water-partially soluble or water-swellable cellulose include crystalline cellulose, crystalline cellulose sodium carmellose, ethylcellulose, low-substituted hydroxypropylcellulose hydroxypropy methylcellulose phthalate, hydroxypropyl-methylcellulose acetate succinate, carmellose, carmellose calcium, cross carmellose sodium, carboxydimethyl-ethylcellulose, cellulose acetate phthalate and the like.

The celluloses which may be used preferably in the present invention are carmellose sodium, methylcellulose, hydroxypropylcellulose and hydroxypropylmethylcellulose. Among them, carmellose sodium is more preferable from the standpoint that it shows a high tendency to give spherical powder particles.

Although the amount used of cellulose may be varied depending on the kind and amount of emulsifying agent to be used, it may be generally 0.1–20% by weight, preferably 0.1–10% by weight, based on the total weight of powder composition to be fed.

In case where an emulsion is prepared by emulsifying an oil containing tocotrienol with a lecithin, a cellulose and an emulsifying agent in water, the concentration of the emulsion may be 35–45% from the standpoint of emulsification treatment (workability). Otherwise, a water-soluble cellulose and an emulsifying agent are dissolved in water, and then the solution may be combined with a separately prepared mixture of an oil containing tocotrienol and a lecithin for emulsifying treatment.

The condition under which an emulsification treatment is conducted may be varied depending on the kind and the composition ratio of an oil containing tocotrienol to be used and hence it is not limited particularly. However, the emulsification treatment may be usually conducted at room temperature. If necessary, it may be conducted at an adequately elevated temperature.

A stable emulsion may also be prepared by the following method.

That is, an emulsification treatment is accomplished in two steps dividing the total amount of water contained in the suspension to be spray-dried into 2 times, instead of adding it at one stroke.

An emulsifying agent such as gelatin, casein sodium, arabic gum, sodium alginate or the like and a cellulose such as carmellose sodium, hydroxypropylmethylcellulose or the like are dissolved in warm water (at 30–80° C.) whose amount being 1/3–1/2 of the predetermined total amount of water for preparation of a suspension, the solution is mixed with a mixture prepared separately by adding lecithin to an oil containing tocotrienol and the stirring is operated for the preliminary emulsification treatment, after which residual amount of warm water is added and a stirring is operated to allow the emulsification treatment to complete thereby there can be obtained a homogeneous and stable emulsion. The amount added of warm water for the second emulsification treatment is 1–3 times, preferably 2–2.5 times of that used in the first or preliminary emulsification treatment.

If an emulsion having the prescribed concentration has been prepared, then subsequently a powder substance as oil absorbent is added thereto and mixed together, and the resultant suspension is subjected to spray drying.

The powder substance is a carrier which is capable of adhering or absorbing an oil containing tocotrienol. Examples of such powders include inorganic ones such as calcium silicate, soft silicic anhydride, magnesium alumino metasilicate, calcium hydrogen phosphate and the like, and organic ones such as dextrin and the like. The preferred powder is calcium silicate (a specific calcium silicate porous powder, a trade name "Florite", a product of Tokuyama Soda Co., Ltd.). It is a porous powder having an apparent specific gravity of 10–11 ml/g, a liquid absorption amount of 5–6 ml/g and an excellent compressibility.

The amount used of the powder substance as absorbent may be varied depending on the amount of an oil containing tocotrienol to be used, the amounts of a lecithin and a cellulose to be incorporated, thus it is not limited particularly.

However, it may be 0.1–99% by weight per weight of the tocotrienol-containing powder to be formed.

In preparing the tocotrienol-containing powder, lactose may be further added as solubilizing auxiliary material in addition to the foregoing constituent ingredients.

As to the concentration of a suspension (the second emulsion) to be spray-dried, typically 8–15% by weight is preferable. This suspension gives a stable emulsion by mere stirring procedure so that any phase separation does not occur even on standing for 3 days at a temperature of 50° C.

The temperature at which spray drying is conducted may be varied depending on the drying condition, raw materials to be used and the type of spray-drier to be used, thus it is not limited particularly. In case of, for example, a spray drier (atomizer type), generally spray-drying may be conducted at an inlet temperature ranging from about 210° C. to about 250° C. and an outlet temperature ranging from about 90° C. to about 120° C. according to the conventional method.

Also, the suspension (the second emulsion) to be spray-dried may be subjected to spray-drying and granulation or to freeze-drying and hot air drying placing the freeze-dried material on the fluidized bed for preparing granular product.

The thus obtained spray-dried powder may be compressed into a tablet form according to the conventional method. As shown in Examples described later, if it compressed under a compression pressure of 100–750 kgf/cm$^2$, there may be obtained tablets each having a constant range of hardness without influence of compression pressure.

In preparing industrially tablets using the tocotrienol-containing powder obtained in the present process, there may be employed a lubricant which has been generally known and hitherto used, for example, stearic acid, magnesium stearate, calcium stearate, sugar fatty acid ester, polyethylene glycol, hydrogenized oil, paraffin wax, talc or the like. In a continuous production of tablet containing such a highly concentrated oil component as 40% by weight or more of tocotrienols using, for example, a rotary tablet machine, in some cases there is recognized adhesion of said spray-dried powder to a pounder and a mortar phenomenon caused by occurrence of a membrane of oil components which have migrated into the surface of a turntable. As effective lubricants for preventing these defects, for example one or more of higher fatty acids having 12–24 carbon atoms such as stearic acid, palmitic acid, oleic acid and the like may be used. Among them, especially stearic acid or higher fatty acid wherein the content of stearic acid is high is preferred. In this case, the amount used of higher fatty acid may be 0.2–10%, preferably 1–5% per tablet weight. As to tablet pressure to be applied, it may be 200–1000 kg, preferably 300–500 kg.

Also, a wide variety of drugs may be incorporated into the tocotrienol-containing powder for the purpose of preparing a tablet by a compression molding. Any drugs may be used without particular limitation so long as they are inert to the tocotrienol-containing powder.

THE BEST MODE FOR CARRYING OUT THE INVENTION

The following Examples illustrate the present invention more specifically. Needless to say, the present invention is not limited thereto. The terms "tocotrienol oil" used in Examples and Comparative Examples mean tocotrienol-containing oil as defined in the specification.

EXAMPLE 1

1.0 Gram of lecithin (a product of Wako Pure Chemical Industries, Ltd., soybean lecithin) and 2.0 g of carmellose sodium and 13.75 g of gelatin were dissolved in 400 ml of water. To this solution under vigorous stirring with a homomixer was added 55 g of tocotrienol oil (a product of Eastman Chemical Company, a trade name "NuTriene tocotrienol": total tocotrienol content of 30% by weight) and the vigorous stirring with a homomixer was continued until a homogeneous emulsion was formed. To the resultant emulsion was added 28.25 g of calcium silicate (a product of Tokuyama Soda Co., Ltd., a trade name "Florite RE") while a vigorous stirring with a homomixer was operated. And then, 498 g of the resultant suspension was spray-dried at the inlet temperature of about 220° C. and the outlet temperature of about 108° C., thereby there was obtained 75 g (75.3% yield) of pale yellow powders containing tocotrienol (total tocotrienol content of 16.5%).

Figure 1:
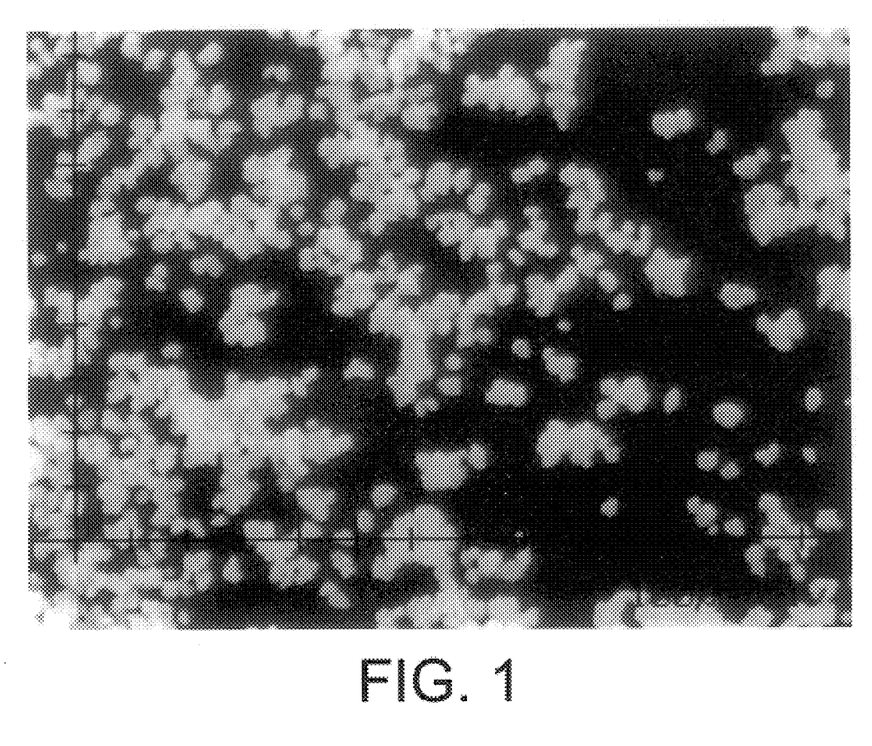
FIG. 1 shows a photograph of the powder obtained in Example 1.

The obtained powders had a moisture content of 1.2%, a static specific volume of 4.10 ml/g, a dynamic specific volume of 3.05 ml/g and an angle of repose of 38°. As be apparent from the photograph shown in FIG. 1, they were spherical particles. (A scale mark appearing in FIG. 1 indicates 100 μm.)

In the following Examples and Comparative Examples, the term "stirring" means a vigorous stirring with a homomixer).

EXAMPLE 2

0.5 Gram of lecithin (a product of Wako Pure Chemical Industries, Ltd., soybean lecithin) and 2.0 g of carmellose sodium and 13.75 g of gelatin were dissolved in 400 ml of water. To this solution under stirring was added 55 g of tocotrienol oil (a product of Oryza Oil & Fat Chemical Co., Ltd., a trade name "Oryzatocotrienol": tocotrienol content of 30% by weight) and the stirring was continued until a homogeneous emulsion was formed. To the resultant emulsion was added 28.75 g of calcium silicate (a trade name "Florite RE") while a stirring was operated. And then, 467 g of the resultant suspension was spray-dried at the inlet temperature of about 215° C. and the outlet temperature of about 108° C., thereby there was obtained 73 g (75.3% yield) of pale yellow powders containing tocotrienol (total tocotrienol content of 16.5%).

The obtained powders had a moisture content of 1.8%, a static specific volume of 3.81 ml/g, a dynamic specific volume of 2.80 ml/g and an angle of repose of 40°.

EXAMPLE 3

2.75 Grams of lecithin (a product of Wako Pure Chemical Industries, Ltd., soybean lecithin) and 0.83 g of carmellose sodium and 13.75 g of gelatin were dissolved in 412 ml of water. To this solution under stirring was added 55 g of tocotrienol oil (a product of Eastman Chemical Company, a trade name "NuTriene tocotrienol": total tocotrienol content of 30% by weight) and the stirring was continued until a homogeneous emulsion was formed. To the resultant emulsion was added 27.67 g of calcium silicate (a trade name "Florite RE") while a stirring was operated. And then, 477 g of the resultant suspension was spray-dried at the inlet temperature of about 210° C.~215° C. and the outlet temperature of about 105° C., thereby there was obtained 63.4 g (63.4% yield) of pale yellow powders containing tocotrienol (total tocotrienol content of 16.5%).

The obtained powders had a moisture content of 1.5%, a static specific volume of 3.92 ml/g, a dynamic specific volume of 2.90 ml/g and an angle of repose of 38°.

EXAMPLE 4

1.0 Gram of lecithin (a product of Wako Pure Chemical Industries, Ltd., soybean lecithin) and 2.0 g of carmellose sodium and 3 g of dextrin (a product of Matsutani Chemical Industry Co., Ltd., a trade name "Pine-dex") were dissolved in 355 ml of water. To this solution under stirring was added 55 g of tocotrienol oil (a product of Oryza Oil & Fat Chemical Co., Inc., a trade name "Oryzatocotrienol": total tocotrienol content of 30% by weight) and the stirring was continued until a homogeneous emulsion was formed. To the resultant emulsion was added 25.25 g of calcium silicate (a trade name "Florite RE") while a stirring was operated. And then, 419 g of the resultant suspension was spray-dried at the inlet temperature of about 225° C. and the outlet temperature of about 108° C., thereby there was obtained 65 g (78.3% yield) of pale yellow powders containing tocotrienol (total tocotrienol content of 16.5%).

The obtained powders had a moisture content of 1.0%, a static specific volume of 3.81 ml/g, a dynamic specific volume of 2.77 ml/g and an angle of repose of 39°.

EXAMPLE 5

1.0 Gram of lecithin (a product of Wako Pure Chemical Industries, Ltd., soybean lecithin), 2.0 g of carmellose sodium 13.75 g of gelatin and 3 g of dextrin (a product of Matsutani Chemical Industry Co., Ltd., a trade name "Emulstar #30A") were dissolved in 354 ml of water. To this solution under stirring was added 55 g of tocotrienol oil (a product of Eastman Chemical Company, a trade name "NuTrient tocotrienol": total tocotrienol content of 30% by weight) and the stirring was continued until a homogeneous emulsion was formed. To the resultant emulsion was added 25.25 g of calcium silicate (a trade name "Florite RE") while a stirring was operated. And then, 377 g of the resultant suspension was spray-dried at the inlet temperature of about 225° C. and the outlet temperature of about 109° C., thereby there was obtained 65 g (78.3% yield) of pale yellow powders containing tocotrienol (total tocotrienol content of 16.5%).

The obtained powders had a moisture content of 1.2%, a static specific volume of 3.81 ml/g, a dynamic specific volume of 2.80 ml/g and an angle of repose of 40°.

EXAMPLE 6

1.0 Gram of lecithin (a product of Wako Pure Chemical Industries, Ltd., soybean lecithin) and 5.0 g of hydroxypropylmethyl cellulose 13.75 g of gelatin and 3 g of dextrin (a product of Matsutani Chemical Industry Co., Ltd., a trade name "Pine-dex") were dissolved in 355 ml of water. To this solution under stirring was added 55 g of tocotrienol oil (a product of Oryza Oil & Pat Chemical Co., Inc., a trade name "Oryzatocotrienol": total tocotrienol content of 30% by weight) and the stirring was continued until a homogeneous emulsion was formed. To the resultant emulsion was added 22.25 g of calcium silicate (a trade name "Florite RE") while a stirring was operated. And then, 419 g of the resultant suspension was spray-dried at the inlet temperature of about 225° C. and the outlet temperature of about 108° C., thereby there was obtained 66 g (79.5% yield) of pale yellow powders containing tocotrienol (total tocotrienol content of 16.5%).

The obtained powders had a moisture content of 1.2%, a static specific volume of 4.04 ml/g, a dynamic specific volume of 3.01 ml/g and an angle of repose of 37°.

EXAMPLE 7

1.5 Gram of lecithin (a product of Wako Pure Chemical Industries, Ltd., soybean lecithin) and 1.6 g of carmellose sodium and 16 g of gelatin were dissolved in 354 ml of water. To this solution under stirring was added 58 g of tocotrienol oil (a product of Golden Hope Plantations Berhad: total tocotrienol content of 70% by weight) and the stirring was continued until a homogeneous emulsion was formed. To the resultant emulsion was added 22.9 g of calcium silicate (a trade name "Florite RE") while a stirring was operated. And then, 454 g of the resultant suspension was spray-dried at the inlet temperature of about 210° C.~215° C. and the outlet temperature of about 105° C., thereby there was obtained 73.1 g (73.1% yield) of pale yellow powders containing tocotrienol (total tocotrienol content of 40%).

The obtained powders had a moisture content of 1.2%, a static specific volume of 4.20 ml/g, a dynamic specific volume of 3.22 ml/g and an angle of repose of 40°.

EXAMPLE 8

1.25 Kilogram of gelatin and 125 g of carmellose sodium were dissolved in 12 kg of warm water, and to this solution was added 90 g of lecithin after mixing with 5.0 kg of tocotrienol oil (a product of Eastman Chemical Company, total tocotrienol content of 30% by weight) under stirring. And the stirring was continued until a homogeneous emulsion was formed. 20 Kilograms of warm water was further added thereto and stirred to allow the emulsification to complete.

To the resultant emulsion was added 2.625 kg of calcium silicate (a trade name "Florite RE") under stirring. And then, 41.3 kg of the resultant suspension was spray-dried at the inlet temperature of about 210° C.~220° C. and the outlet temperature of about 150° C., thereby there was obtained 8.16 kg (89.8% yield) of pale yellow powders containing tocotrienol (total tocotrienol content of 16.5%)

The obtained powders had a moisture content of 1.59%, a static specific volume of 4.73 ml/g, a dynamic specific volume of 3.70 ml/g and an angle of repose of 33°.

EXAMPLE 9

1.25 Kilogram of gelatin and 125 g of carmellose sodium were dissolved in 12 kg of warm water, and to this solution was added 90 g of lecithin after mixing 5.0 kg of tocotrienol oil (a product of Carotech Sdn Bhd., total tocotrienol content of 30% by weight) under stirring. The resultant mixture was subjected to an emulsification treatment. 29 Kilograms of warm water was further added thereto and stirred to allow the emulsification to complete. To the resultant emulsion was added 2.625 kg of calcium silicate (a trade name "Florite RE") under stirring thereby obtaining 50 kg of a suspension. And then, the suspension was spray-dried at the inlet temperature of about 190° C.~195° C. and the outlet temperature of about 140° C., thereby there was obtained 8.08 kg (88.9% yield) of pale yellow powders containing tocotrienol (total tocotrienol content of 16.5%).

The obtained powders had a moisture content of 0.98%, a static specific volume of 4.81 ml/g, a dynamic specific volume of 3.59 ml/g and an angle of repose of 39°.

EXAMPLE 10

1.4 Kilogram of gelatin and 140 g of carmellose sodium were dissolved in 13 kg of warm water, and to this solution was added 125 g of lecithin after mixing with 5.0 kg of tocotrienol oil (a product of Carotech Sdm Bhd., total tocotrienol content of 50% by weight) under stirring. The stirring was continued until a homogeneous emulsion was formed. 25 Kilograms of warm water was further added thereto and stirred to allow the emulsification to complete. To the resultant emulsion was added 1.665 kg of calcium silicate (a trade name "Florite RE") under stirring thereby obtaining 46.27 kg of a suspension. And then, the suspension was spray-dried at the inlet temperature of about 200° C.~210° C. and the outlet temperature of about 150° C., thereby there was obtained 6.08 kg (73.0% yield) of pale yellow powders containing tocotrienol (total tocotrienol content of 30%).

The obtained powders had a moisture content of 0.81%, a static specific volume of 4.18 ml/g, a dynamic specific volume 3.00 ml/g and an angle of repose of 38°.

EXAMPLES 11~14

There were obtained powders containing tocotrienol according to the similar manner as in Example 1 except that the kind of tocotrienol oil, lecithin, emulsifying agent, powder material and cellulose as well as their compounding ratios were varied.

The results are as shown below in table 1.

TABLE 1

| | | | | | | | Powder | |
| --- | --- | --- | --- | --- | --- | --- | --- | --- |
| Ex. No. | TC (g) | LE (g) | Emulsifying Agent (g) | Powder Material (g) | CMC—Na (g) | Slurry (ml) | Yield (%) | Specific Volume Static/Dynamic (ml/g) | Angle of Repose (°) |
| 11 | 50 | 0.5 | G: 15.0 A: 10.0 D: 22.7 | FR: 1.8 | 1.8 | 286 | 63.4 | 3.81/2.80 | 40 |
| 12 | 60 | 1.1 | E#30: 18 | FR: 19.1 | 2.0 | 455 | 75.4 | 4.20/3.20 | 40 |
| 13 | 55 | 1.0 | EA: 13.8 | FR: 28.25 | 2.0 | 455 | 80.0 | 4.02/3.11 | 39 |
| 14 | 55 | 1.0 | E#30: 13.75 | FR: 28.25 | 2.0 | 500 | 84.3 | 4.01/3.12 | 40 |

In table 1, TC indicates tocotrienol oil, LE does lecithin, G does gelatin, A does arabic gum, D does dextrin, E# does a modified starch "Emulstar E#" (a trade name, a product of Matsutani Chemical Industry Co., Ltd.), EA does a modified starch "Emulstar A" (a trade name, a product of Matsutani Chemical Industry Co., Ltd.), FR does calcium silicate "Florite RE" and CMC—Na does carmellose sodium.

The terms "slurry (ml)" indicate the volume of the slurry obtained finally in the emulsification step, and the terms "yield (%)" do the yield of the powder obtained from the slurry by spray drying.

EXAMPLE 15

1.5 Gram of lecithin (a product of Wako Pure Chemical Industries, Ltd., soybean lecithin) and 1.6 g of carmellose sodium and 16 g of gelatin were dissolved in 354 ml of water. To this solution under stirring was added 58 g of tocotrienol oil (a product of Golden Hope Plantations Berhad: total tocotrienol content of 70% by weight) and stirring was continued until a homogeneous emulsion was formed. To the resultant emulsion was added 23.0 g of magnesium alumino metasilicate (a trade name "Neusilin", a product of Fuji Chemical Industry Co., Ltd.) while a stirring was operated. And then, 454 g of the resultant suspension was spray-dried at the inlet temperature of about 210° C.~215° C. and the outlet temperature of about 105° C., thereby there was obtained 73.2 g (73.2% yield) of pale yellow powders containing tocotrienol (total tocotrienol content of 40%).

The obtained powders had a moisture content of 1.2%, a static specific volume of 3.48 ml/g, a dynamic specific volume of 2.40 ml/g and an angle of repose of 36°.

EXAMPLE 16

1.5 Gram of lecithin (a product of Wako Pure Chemical Industries, Ltd., soybean lecithin) and 1.6 g of carmellose sodium and 16 g of gelatin were dissolved in 354 ml of water. To this solution under stirring was added 58 g of tocotrienol oil (a product of Golden Hope Plantations Berhad: total tocotrienol content of 70% by weight) and the stirring was continued until a homogeneous emulsion was formed. To the resultant emulsion was added 23.0 g of silicic anhydride while a stirring was operated. And then, 454 g of the resultant suspension was spray-dried at the inlet temperature of about 210° C.~215° C. and the outlet temperature of about 105° C., thereby there was obtained 73.1 g (73.1% yield) of pale yellow powders containing tocotrienol (total tocotrienol content of 40%).

The obtained powders had a moisture content of 1.0%, a static specific volume of 2.56 ml/g, a dynamic specific volume of 2.26 ml/g and an angle of repose of 32°.

EXAMPLE 17

0.625 Kilogram of gelatin and 63 g of carmellose sodium were dissolved in 5 Kg of warm water, and to the solution was added 45 g of lecithin after mixing with 2.5 kg of tocotrienol oil (a product of Eastman Chemical Company, total tocotrienol content of 30% by weight) under stirring. And the stirring was continued until a homogeneous emulsion was formed. 25 Kilograms of warm water was further added thereto and stirred to allow the emulsification to complete.

To the resultant emulsion was added 6.767 kg of calcium hydrogen phosphate (a trade name "Fujicalin", a product of Fuji Chemical Industry Co., Ltd.) under stirring to obtain 40.4 kg of a suspension, which was spray-dried at the inlet temperature of about 210° C.~230° C. and the outlet temperature of about 120° C.~140° C., thereby there was obtained 9.3 kg (95.0% yield) of pale yellow powders containing tocotrienol (total tocotrienol content of 7.5%

The obtained powders had a moisture content of 0.8%, a static specific volume of 2.57 (ml/g) and an angle of repose of 35°.

EXAMPLE 18

0.45 Kilogram of gelatin and 45 g of carmellose sodium were dissolved in 3.7 kg of warm water, and to the solution was added 40 g of lecithin after mixing with 1.5 kg of tocotrienol oil (a product of Carotech Co., Sdn Bhd., total tocotrienol content of 50% by weight) under stirring. And the stirring was continued until a homogeneous emulsion was formed. 26.3 Kilograms of warm water was further added thereto and stirred to allow the emulsification to complete. To the resultant emulsion was added 7.965 kg of calcium hydrogen phosphate (a trade name "Fujicalin", a product of Fuji Chemical Industry Co., Ltd.) under stirring to obtain 40.4 kg of a suspension, which was spray-dried at the inlet temperature of about 210° C.~230° C. and the outlet temperature of about 120° C.~140° C., thereby there was obtained 9.5 kg (96.0% yield) of pale yellow powders containing tocotrienol (total tocotrienol content of 7.5%).

EXAMPLE 19

0.8 Kilogram of gelatin and 80 g of carmellose sodium were dissolved in 6.5 kg of warm water, and to the solution was added 70 g of lecithin after mixing with 2.86 kg of tocotrienol oil (a product of Golden Hope Plantations Berhad, total tocotrienol content of 70% by weight) under stirring. And the stirring was continued until a homogeneous emulsion was formed. 23.5 Kilograms of warm water was further added thereto and stirred to allow the emulsification to complete. To the resultant emulsion was added 6.19 kg of calcium hydrogen phosphate (a trade name "Fujicalin", a product of Fuji Chemical Industry Co., Ltd.) under stirring to obtain 40.4 kg of a suspension, which was spray-dried at the inlet temperature of about 210° C.~230° C. and the outlet temperature of about 120° C.~140° C., thereby there was obtained 8.0 kg (81.5% yield) of pale yellow powders containing tocotrienol (total tocotrienol content of 20.0%).

The obtained powders had a moisture content of 0.9%, a static specific volume of 2.8 (ml/g) and an angle of repose of 38°.

EXAMPLE 20

13.75 Grams of modified starch ("a trade name "Emulstar 30A") and 2.0 g of carmellose sodium were dissolved in 28 ml of warm water, and to the solution was added 1.0 g of lecithin after mixing with 55 g of tocotrienol oil (a product of Eastman Chemical Company, total tocotrienol content of 30% by weight) under stirring. And the stirring was continued until a homogeneous emulsion was formed. 265 Grams of warm water was further added thereto and stirred to allow the emulsification to complete. To the resultant emulsion was added 28.25 g of calcium silicate (a trade name "Florite") under stirring to obtain 455 g of a suspension, which was spray-dried at the inlet temperature of about 225° C.~230° C. and the outlet temperature of about 107° C.~114° C., thereby there was obtained 80.0 g (80.0% yield) of pale yellow powders containing tocotrienol (total tocotrienol content of 16.5%).

The obtained powders had a moisture content of 1.0%, a static specific volume of 3.77 ml/g, a dynamic specific volume of 2.70 ml/g and an angle of repose of 38°.

EXAMPLE 21

0.5 Gram of lecithin (a product of Wako Pure Chemical Industries, Ltd., soybean lecithin) and 1 g of carmellose sodium and 5 g of casein sodium were dissolved in 354 ml of water. To this solution under stirring was added 65 g of tocotrienol oil (a product of Golden Hope Plantations Berhad: total tocotrienol content of 70% by weight) and the stirring was continued until a homogeneous emulsion was formed. To the resultant emulsion was added 18.5 g of silicic anhydride while a stirring was operated. And then, 454 g of the resultant suspension was spray-dried at the inlet temperature of about 210° C.~215° C. and the outlet temperature of about 105° C., thereby there was obtained 74 g (74% yield) of pale yellow powders containing tocotrienol (total tocotrienol content of 45.5%).

The obtained powders had a moisture content of 1.0%, a static specific volume of 2.55 ml/g, a dynamic specific volume of 2.25 ml/g and an angle of repose of 33°.

EXAMPLE 22

1.89 Kilogram of casein sodium (a product of Nippon Protein Co., Ltd., a trade name "ALANATE 180"), 5.67 kg of gelatin and 0.63 kg of carmellose sodium were dissolved in 55 liters of warm water (60° C.), and to the solution was added 0.45 g of lecithin (a trade name "SLP PASTE") after mixing with 27.0 kg of tocotrienol oil (a product of Carotech Sdn Bhd., a trade name "TOCOMIN 50", 50% content) under stirring.

And the stirring was continued until a homogeneous emulsion was formed. 104 Liters of warm water was further added thereto and stirred to allow the emulsification to complete.

To the resultant emulsion was added 9.32 kg of calcium silicate (a trade name "Florite RE") under stirring to obtain 204 kg of a suspension, which was spray-dried at the inlet temperature of about 220° C.~230° C. and the outlet temperature of about 142° C.~148° C., thereby there was obtained 39.5 kg (88% yield) of pale yellow powders containing tocotrienol (total tocotrienol content of 30.0%).

The obtained powders had a moisture content of 1.08%, a static specific volume of 4.57 ml/g, a dynamic specific volume of 3.41 ml/g, and an angle of repose of 40.5°.

EXAMPLE 23

1.4 Kilogram of casein sodium (a trade name of "SODIUM CASEINATE", a product of EMV) and 0.14 kg of carmellose sodium (a trade name of "CMC Daicel" a product of Daicel Chemical Industry Co., Ltd.) were dissolved in 11.3 L of warm water (50° C.), and to the solution was added a mixed solution of 0.05 kg of lecithin (soybean lecithin, a trade name of "SLP Paste SP", a product of True Lecithin Industry Co, Ltd.) and 5.80 kg of tocotrienol oil (a product of Golden Hope Plantations Berhad, total tocotrienol content of 70% by weight) under stirring. And the stirring was continued until a homogeneous emulsion was formed. 28.7 L of warm water (50° C.) was further added thereto and stirred to allow the emulsification to complete. To the resultant emulsion was added 2.21 kg of calcium silicate (a trade name "Florite RE") and 0.40 kg of crystalline cellulose (a trade name of "Avicel FD-101, a product of Asahi Chemical Industry Co., Ltd.) under stirring to prepare a suspension (total weight of 50 kg), which was spray-dried at the inlet temperature of about 200° C.~230° C. and the outlet temperature of about 135° C.~155° C., thereby there was obtained 9.2 kg (92.0% yield) of pale yellow powders containing tocotrienol (total tocotrienol content of 40%).

The obtained powders had a moisture content of 0.8%, a static specific volume of 4.44 ml/g, a dynamic specific volume of 3.40 ml/g, and an angle of repose of 38°.

COMPARATIVE EXAMPLE 1

A similar procedure was conducted as in Example 1 except that no lecithin was compounded.

That is, 2.0 g of carmellose sodium and 13.75 g of gelatin were dissolved in 400 ml of water. To this solution under stirring was added 55 g of tocotrienol oil (a product of Eastman Chemical Company, a trade name "NuTriene tocotrienol": tocotrienol content of 30% by weight) and the stirring was continued until a homogeneous emulsion was formed. To the resultant emulsion was added 28.25 g of calcium silicate (a trade name "Flolite RE") while a stirring was operated. And then, 498 g of the resultant suspension was spray-dried at the inlet temperature of about 220° C. and the outlet temperature of about 108° C., thereby there was obtained 60 g (60% yield) of pale yellow powders containing tocotrienol. However, there can not be obtained spherical particle. The product had a tackiness owing to oil bleeding. And therefore, a large amount of the powder adhered to the wall of the spray-dryer.

The pale yellow powders containing tocotrienol which were prepared in Examples 1~22 had no tackiness and retained free flowability. There was not recognized any adhesion of the powder to the wall of the spray-dryer during its preparation step and any troubles in its recovery procedure. Also, it did not cake and any aggregated lumps were not present in the powder even when stored for 3 months at a relative humidity of 80% and room temperature.

Furthermore, each of the slurry (suspensions) prepared in Examples 1~22 was homogenous and showed a good stability in emulsification so that almost no separation of an oil phase generated even when it was allowed to stand, for example for about 3 days at 50° C.

As a result of evaluation by HPLC of the ingredients in the respective powders obtained in the above-mentioned Examples, the original tocotrienol content in the starting material was maintained, showing that tocotrienol did not decompose during the preparation step for the powder.

Tablets were made using the powder prepared in Example 1 or 4 to evaluate their usefulness from the relationship between the compression pressure under which tablets were made and the hardness of the resultant tablets.

TABLET PREPARATION EXAMPLE 1

500 Mg of the powder prepared in Example 1 or 4 wherein the total tocotrienol content was 16.5% was mixed with 1 mg of magnesium stearate, and the mixture was compressed into a tablet form using a single tablet hydraulic machine Tableting Tester-SK-02 (a product of Sankyo Piotech Co., Ltd.) (the diameter of the tablet in this case was 11.3 mm). (The relationship between the compression pressure under which tablets were made and the tablet hardness)

The results of tablets prepared using each of powders of Examples 1 and 4 are shown in tables 2 and 3, respectively.

TABLE 2

| Tableting Test No. | Compression Pressure kgf | Tablet Hardness kg/= | Tablet Thickness mm |
|---|---|---|---|
| 1 | 100 | 9.0 | 4.5 |
| 2 | 250 | 10.7 | 4.2 |
| 2 | 500 | 10.9 | 4.1 |
| 3 | 750 | 10.8 | 4.0 |

TABLE 3

| Tableting Test No. | Compression Pressure kgf | Tablet Hardness kg/= | Tablet Thickness mm |
|---|---|---|---|
| 4 | 100 | 7.9 | 4.4 |
| 5 | 250 | 8.3 | 4.2 |
| 6 | 500 | 8.4 | 4.1 |
| 7 | 750 | 8.0 | 4.1 |

It is understood from the above results that the tocotrienol-containing powder of the present invention is characterized by that it gives the tablet having approximately constant value in hardness when compressed into a tablet from (500 mg in weight and 11.3 mm in diameter) under a wide range of pressure of 100 kgf~750 kgf. Then, there may be easily obtained the tablet having a hardness enough for practical use even by application of a low pressure and hence it is very advantageous in the case where it is applied to a wide variety of uses.

TABLET PREPARATION EXAMPLE 2

98 Parts by weight of the powder obtained in Example 11 wherein the total tocotrienol content was 7.5% was mixed with 2 parts by weight of stearic acid ("180P-5", a product of Nippon & FATS Co., Ltd.), and the mixture was compressed to form tablets each having 300 mg in weight and 8.0 mm-9R in diameter of tablet metal mold using a rotary tablet machine ("HT-AP18SS-11 type, a product of Hata Iron Works Co., Ltd.). There was obtained tablets each having a hardness of 4 kg by setting the molding pressure during the compression to 550 kgf whereupon there was not recognized tablet trouble such as sticking or bleeding of the oil component into the surface of the machineries such as a pounder, a mortar, a turntable and the like.

COMPARATIVE EXAMPLE 2

99 Parts by weight of the powder obtained in Example 11 wherein the total tocotrienol content was 7.5% was mixed with 1 parts by weight of magnesium stearate (a product of Nippon & FATS Co., Ltd.), and the mixture was compressed to prepare tablets each having 300 mg in weight and 8.0 mm-9R in diameter of tablet metal mold using a rotary tablet machine ("HT-AP18SS-11 type, a product of Hata Iron Works Co., Ltd.). There was obtained tablets each having a hardness of 4 kg by setting the molding pressure during the compression to 1000 kgf whereupon sticking occurred and there was recognized adhesion of the powder to each of a pounder, a mortar and a turntable.

TABLET PREPARATION EXAMPLE 3

98 Parts by weight of the powder obtained in Example 12 wherein the total tocotrienol content was 7.5% was mixed with 2 parts by weight of stearic acid ("180P-5", a product of Nippon & FATS Co., Ltd.), and the mixture was compressed to form tablets each having 300 mg in weight and 8.0 mm-9R in diameter of tablet metal mold using a rotary tablet machine ("HT-AP18SS-11 type, a product of Hata Iron Works Co., Ltd.). There was obtained tablets each having a hardness of 8 kg by setting the molding pressure during the compression to 550 kgf. And, there was obtained tablets each having a hardness 11.4 kg by increasing the molding pressure during the compression from 550 kgf to 1000 kgf. Thus the tablet hardness was increased depending on molding pressure. In either case, there was not recognized tablet trouble such as sticking or bleeding of the oil component into the surface of the machineries such as a pounder, a mortar, a turntable and the like.

TABLET PREPARATION EXAMPLE 4

62.5 Parts by weight of the powder obtained in Example 13 wherein the total tocotrienol content was 20%, 10 parts by weight of partially alpha starch ("PCS", a product of Asahi Chemical Industry Co., Ltd.), 25.5 parts by weight of crystalline starch ("Avicel PH-101", a product of Asahi Chemical Industry Co., Ltd.) and 2 parts by weight of stearic acid ("180P-5", a product of Nippon & FATS Co., Ltd.) were mixed sufficiently and the mixture was compressed to prepare tablets each having 400 mg in weight (each containing total tocotrienol of 50 mg) and 9.5 mm-9R in diameter of tablet metal mold using a rotary tablet machine ("HT-AP18SS-11 type, a product of Hata Iron Works Co., Ltd.). There was obtained tablets each having a hardness of 5 kg by setting the molding pressure during the compression to 700 kgf. And, there was obtained tablets each having a hardness 6.4 kg by increasing the molding pressure during the compression from 550 kgf to 1000 kgf. In this case, the powder for tableting had a good flowability and there was not recognized tablet troubles such as sticking or bleeding of the oil component into the surface of the machineries such as a pounder, a mortar, a turntable and the like.

TABLET PREPARATION EXAMPLE 5

500 mg of the powder obtained in Example 7 wherein the total tocotrienol content was 40% was mixed with 1 mg of magnesium stearate, and then the mixture was compressed into a tablet form using the same tablet machine as in Tablet Preparation Example 1.

Storage Stability Test for Tablet

The test was conducted according to the following method.

The tablets prepared in Tablet Preparation Example 5 were placed in a sample jar having a rubber stopper. After stoppering the sample jar was stored for 1 to 3 months under the condition of a temperature of 40° C. and a relative humidity of 75%.

The tocotrienol content in a tablet was measured every month. As the result, 90% of the original tocotrienol content remained even after storage for 3 months.

Also, the storage stability was further improved by conducting the stoppering step for the sample jar containing the tablets under an atmosphere of nitrogen.

The tocotrienol-containing powder of the present invention may be molded into the compression molded article such as tablet thereby adequately varying the finished form suited to excipient, medicines, foods, cosmetics, feed, functional food, healthy food, nutrient reinforcing agent, neutraceutical and the like. For example, powder, pill, capsule and tablet for medical use may be prepared using the conventional additives such as an excipient, a disintegrator, a lubricant, a binder, a surface active agent, a plasticizer and the like.

INDUSTRIAL APPLICABILITY

As explained above, according to the present invention there may be prepared a tocotrienol-containing powder having a good powder form-retaining property and a free flowability without accompanying adhesion of it to the wall of spray drier used by an industrially simple and convenient spray-drying method. Even when it was stored for a long period of term, there is not recognized such troubles that an oil present in it migrates into its surface to cause an aggregation. Furthermore, if it is subjected to compression molding for preparing tablets using a higher fatty acid having 12~24 carbon atoms such as stearic acid as a lubricant, then it has advantages that there may be tablets efficiently obtained from one wherein tocotrienol content is high and that its utilization range may be expanded to medicines, foods, functional food, healthy food, cosmetics, resin composition, feed and the like, and hence it is industrially very useful.

What is claimed is:

1. A tocotrienol-containing powder prepared by a process which comprises treating an oil containing a tocotrienol with a lecithin, a cellulose and an emulsifying agent in water to form an emulsion, said emulsifying agent being one or more elements selected from the group consisting of the gelatin, casein sodium, arabic gum, sodium alginate and modified starch, mixing the formed emulsion with a powder substance to form a suspension and spray-drying the formed suspension.

2. The tocotrienol-containing powder claimed as in claim 1 which comprises 0.1~3.0% by weight of a lecithin, 0.1~10% by weight of a cellulose, 0.1~30% by weight of an emulsifying agent, 0.1~75% by weight of an oil containing tocotrienol and 0.1~99% by weight of a powder substance.

3. The tocotrienol-containing powder claimed as in claim 1 which comprises 0.5~3.0% by weight of a lecithin, 1~10% by weight of a cellulose, 10~30% by weight of an emulsifying agent, 30~75% by weight of an oil containing tocotrienol and 10~50% by weight of a powder substance.

4. The tocotrienol-containing powder claimed as in claim 3 wherein said cellulose is one or more of elements selected from the group consisting of carmellose sodium, methylcellulose, hydroxypropylcellulose and hydroxypropylmethylcellulose.

5. The tocotrienol-containing powder claimed as in claim 3 wherein said lecithin is one or more of elements selected from the group consisting of vegetable lecithin, fractionated lecithin, yolk lecithin, enzyme-treated lecithin and enzyme-decomposed lecithin.

6. The tocotrienol-containing powder claimed as in claim 3 wherein said powder substance is one or more of elements selected from the group consisting of calcium silicate, soft silicic anhydride, magnesium alumino metasilicate, calcium hydrogen phosphate and dextrin.

7. A process for preparing a tocotrienol-containing powder which comprises dissolving or suspending a lecithin, a cellulose and an emulsifying agent in water, adding an oil containing a tocotrienol to the solution or suspension under a stirring to form an emulsion, mixing an powder substance with the formed emulsion to form a suspension and spray-drying the formed suspension.

8. A tablet comprising the tocotrienol-containing powder claimed in claim 6 said powder being compressed into tablet form.

9. The tablet claimed in claim 8 wherein compression molding has been conducted using a higher fatty acid having 12~24 carbon atoms as a lubricant.

10. The tocotrienol-containing powder claimed as in claim 2 wherein said cellulose is one or more of elements selected from the group consisting of carmellose sodium, methylcellulose, hydroxypropylcellulose and hydroxypropylmethylcellulose.

11. The tocotrienol-containing powder claimed as in claim 1 wherein said cellulose is one or more of elements selected from the group consisting of carmellose sodium, methylcellulose, hydroxypropylcellulose and hydroxypropylmethylcellulose.

12. The tocotrienol-containing powder claimed as in claim 2 wherein said lecithin is one or more of elements selected from the group consisting of vegetable lecithin, fractionated lecithin, yolk lecithin, enzyme-treated lecithin and enzyme-decomposed lecithin.

13. The tocotrienol-containing powder claimed as in claim 1 wherein said lecithin is one or more of elements selected from the group consisting of vegetable lecithin, fractionated lecithin, yolk lecithin, enzyme-treated lecithin and enzyme-decomposed lecithin.

14. The tocotrienol-containing powder claimed as in claim 2 wherein said powder substance is one or more of elements selected from the group consisting of calcium silicate, soft silicic anhydride, magnesium alumino metasilicate, calcium hydrogen phosphate and dextrin.

15. The tocotrienol-containing powder claimed as in claim 1 wherein said powder substance is one or more of elements selected from the group consisting of calcium silicate, soft silicic anhydride, magnesium alumino metasilicate, calcium hydrogen phosphate and dextrin.

16. A tablet comprising the tocotrienol-containing powder claimed in claim 15 said powder being compressed into tablet form.

17. The tablet claimed in claim 16 wherein compression molding has been conducted using a higher fatty acid having 12~24 carbon atoms as a lubricant.

18. A tablet comprising the tocotrienol-containing powder claimed in claim 13 said powder being compressed into tablet form.

19. The tablet claimed in claim 18 wherein compression molding has been conducted using a higher fatty acid having 12~24 carbon atoms as a lubricant.

20. A tablet comprising the tocotrienol-containing powder claimed in claim 11 said powder being compressed into tablet form.

21. The tablet claimed in claim 20 wherein compression molding has been conducted using a higher fatty acid having 12~24 carbon atoms as a lubricant.

22. A tablet comprising the tocotrienol-containing powder claimed in claim 2 said powder being compressed into tablet form.

23. The tablet claimed in claim 22 wherein compression molding has been conducted using a higher fatty acid having 12~24 carbon atoms as a lubricant.

24. A tablet comprising the tocotrienol-containing powder claimed in claim 1 said powder being compressed into tablet form.

25. The tablet claimed in claim 24 wherein compression molding has been conducted using a higher fatty acid having 12~24 carbon atoms as a lubricant.

* * * * *